(12) United States Patent
Hofmann et al.

(10) Patent No.: US 9,446,203 B2
(45) Date of Patent: Sep. 20, 2016

(54) NEEDLE HUB AND DISPOSAL DEVICE FOR SINGLE-USE NEEDLE ASSEMBLIES

(71) Applicants: Verena Hofmann, Frankfurt am Main (DE); Uwe Dasbach, Frankfurt am Main (DE); Peter Nober, Rommersheim (DE); Leo Zeimetz, Buttelborn (DE); Thorsten Mutter, Dorsheim (DE)

(72) Inventors: Verena Hofmann, Frankfurt am Main (DE); Uwe Dasbach, Frankfurt am Main (DE); Peter Nober, Rommersheim (DE); Leo Zeimetz, Buttelborn (DE); Thorsten Mutter, Dorsheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 174 days.

(21) Appl. No.: 14/354,208

(22) PCT Filed: Oct. 30, 2012

(86) PCT No.: PCT/EP2012/071433
§ 371 (c)(1),
(2) Date: Apr. 25, 2014

(87) PCT Pub. No.: WO2013/064476
PCT Pub. Date: May 10, 2013

(65) Prior Publication Data
US 2014/0303570 A1   Oct. 9, 2014

(30) Foreign Application Priority Data
Oct. 31, 2011 (EP) .................................... 11187238

(51) Int. Cl.
*A61M 5/32* (2006.01)
*A61B 17/34* (2006.01)

(52) U.S. Cl.
CPC ........ *A61M 5/3205* (2013.01); *A61B 17/3417* (2013.01); *A61B 2017/347* (2013.01); *A61M 2005/3206* (2013.01)

(58) Field of Classification Search
CPC .................... A61B 17/3417; A61B 2017/347; A61M 2005/3206; A61M 5/3205; A61M 5/321; A61M 2005/3253; A61M 5/3293; A61M 2205/273
See application file for complete search history.

(56) References Cited

U.S. PATENT DOCUMENTS

2008/0255514 A1   10/2008   Crapser

FOREIGN PATENT DOCUMENTS

| EP | 0787501 A2 | 8/1997 |
| WO | 0193924 A1 | 12/2001 |
| WO | 2004030539 A1 | 4/2004 |

*Primary Examiner* — Rebecca E Eisenberg
(74) *Attorney, Agent, or Firm* — Fish & Richardson P.C.

(57) ABSTRACT

Described is a needle hub comprising a proximal end adapted to engage a medicament delivery device, a distal end having an opening, a shoulder disposed between the proximal end and the distal end, and a needle assembly engagement mechanism (F1) coupled to the shoulder and adapted to releasably engage a needle assembly. The needle assembly engagement mechanism (F1) includes two or more resilient arms adapted to releasably engage a retainer element on the needle assembly.

20 Claims, 3 Drawing Sheets

NEEDLE HUB AND DISPOSAL DEVICE FOR SINGLE-USE NEEDLE ASSEMBLIES

CROSS REFERENCE TO RELATED APPLICATIONS

The present application is a U.S. National Phase Application pursuant to 35 U.S.C. §371 of International Application No. PCT/EP2012/071433 filed Oct. 30, 2012, which claims priority to European Patent Application No. 11187238.8 filed Oct. 31, 2011. The entire disclosure contents of these applications are herewith incorporated by reference into the present application.

FIELD OF INVENTION

The invention relates to a needle hub for single-use needles and a disposal device for used single-use needle assemblies.

BACKGROUND

Patients suffering from diseases like diabetes have to frequently self-administer injections. Injection devices like auto-injectors or pen injectors have been developed to facilitate self-administering injections. Typically, such injection devices are fitted with a sterile, disposable needle assembly for each injection to minimize the risk of infections.

A conventional needle assembly consists of a hub for engaging the injection device, a double-tipped needle coupled to the hub, and a spring-biased needle shield for hiding the needle from view and covering an injection end of the needle after the injection. The conventional needle assembly also includes a protective cap to maintain sterility of the needle and prevent against inadvertent actuation. Conventional needle assemblies are often packaged loosely in boxes. Thus, a patient is required to carry a box of the needle assemblies (and a sharps disposal unit) when travelling. Similarly, loosely packing the needle assemblies does not optimally use packing space available. Thus, there is a need for a single-use needle assembly.

Further, a conventional needle assembly typically engages the injection device by threads, requiring the patient to manually engage and disengage the needle assembly and the injection device. However, it may present an injury risk if the patient is required to manually remove a single-use needle, and in any event, it may be difficult for the patient (especially if the patient has dexterity or vision problems) to manipulate the single-use needle. Thus, there is a need for a disposal device for single-use needles.

SUMMARY

It is an object of the present invention to provide a needle hub for single-use needle assemblies.

It is a further object of the present invention to provide a disposal device for single-use needle assemblies that minimizes the risk of accidental needle stick injuries.

In an exemplary embodiment, a needle hub according to the present invention comprises a proximal end adapted to engage a medicament delivery device, a distal end having an opening, a shoulder disposed between the proximal end and the distal end, and a needle assembly engagement mechanism coupled to the shoulder and adapted to releasably engage a needle assembly. The needle assembly engagement mechanism includes two or more resilient arms adapted to releasably engage a retainer element on the needle assembly. In an exemplary embodiment, the proximal end includes a screw thread.

In an exemplary embodiment, the arms include notches adapted to engage the retainer element when the arms are in a non-deflected position.

In an exemplary embodiment, a channel having a first diameter is disposed between the arms. An aperture having a second diameter is formed at a distal end of the arms, wherein the second diameter is greater than the first diameter.

In an exemplary embodiment, the needle hub further comprises a spring disposed between the arms and grounded proximally on the shoulder. The spring is grounded distally on the notches when the arms are in the non-deflected position.

In an exemplary embodiment, the needle hub further comprises a needle having a distal tip and a proximal tip. The retainer element is disposed on the needle. The retainer element has a distal part with a third diameter and a proximal part with a fourth diameter. The third diameter is greater than the fourth diameter. The third diameter is substantially equal to the second diameter and the fourth diameter is substantially equal to the first diameter. The fourth diameter is less than a diameter of the spring. When the needle assembly is retained in the needle hub, the retainer element abuts the distal part of the retainer element abuts the notches.

In an exemplary embodiment, a needle assembly disposal device according to the present invention comprises a housing having a cavity therein, an interface disposed on the housing and having an opening adapted to receive the needle hub, a stem adapted to engage the arms, and a flexible membrane disposed adjacent a base of the stem. The membrane has an expandable aperture. The interface includes alignment features adapted to align the needle hub with the stem.

In an exemplary embodiment, the needle assembly disposal device further comprises a spring applying a biasing force to the stem. The spring is grounded distally on the housing and proximally on a connector coupled to the stem.

In an exemplary embodiment, the needle assembly disposal device further comprises a deflector disposed within the housing and aligned with the stem.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
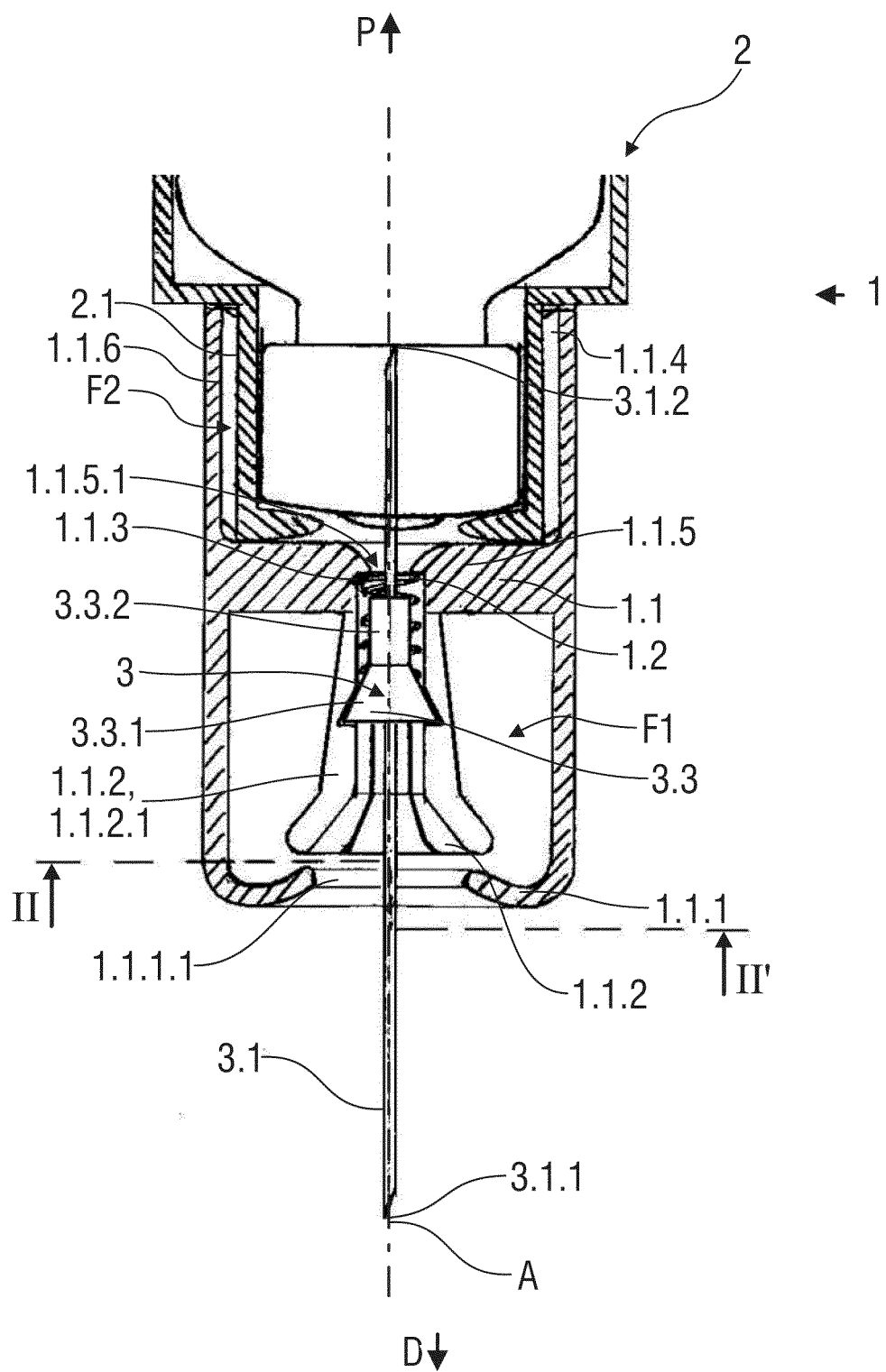
FIG. 1 shows schematically a sectional view of an exemplary embodiment of a needle hub according to the present invention.
Figure 2:
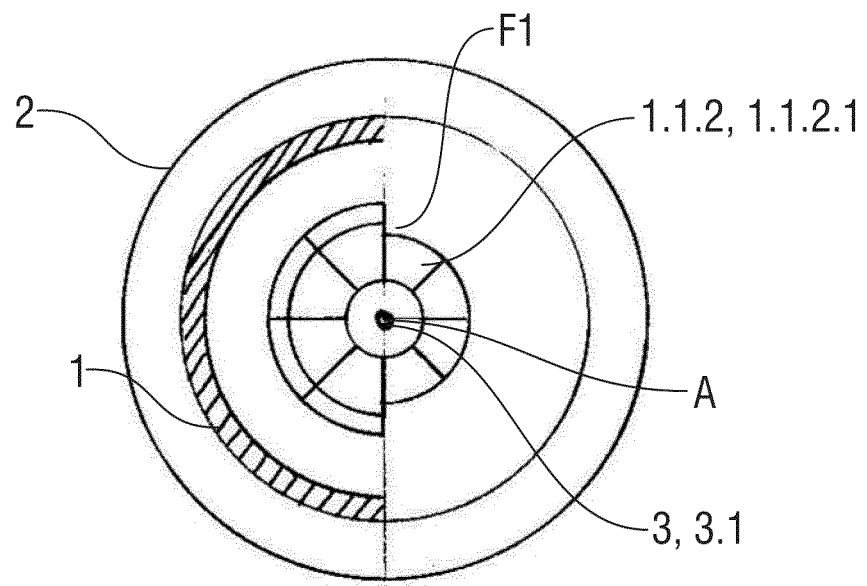
FIG. 2 shows schematically a top view of an exemplary embodiment of a needle hub according to the present invention.

FIGS. 1 and 2 show an exemplary embodiment of a needle hub 1 according to the present invention. The needle hub 1 includes a housing 1.1 which is adapted to engage a medicament delivery device 2. The delivery device 2 may a pen injector, an autoinjector, a syringe, etc. In another exemplary embodiment, the needle hub 1 may be formed integrally with the delivery device 2.

The needle hub 1 is adapted to engage a needle assembly 3 which holds a needle 3.1. In an exemplary embodiment, the needle assembly 3 is a single-use needle assembly which is coupled to the needle hub 1 before use and removed from the needle hub 1 after use. In an exemplary embodiment, the needle assembly 3 includes a retainer element 3.3 which is adapted to engage the needle hub 1. The retainer element 3.3 may include a distal part 3.3.1 having a substantially conical shape and a proximal part 3.3.2 having a substantially cylindrical shape. In an exemplary embodiment, the distal part 3.3.1 has a larger diameter than the proximal part 3.3.2. Those of skill in the art will understand that the retainer element 3.3 may have different sizes and geometries.

In an exemplary embodiment, the housing 1.1 is a hollow cylinder comprising a distal end 1.1.1 and a proximal end 1.1.4, and a shoulder 1.1.5 formed therebetween. The distal end 1.1.1 includes an opening 1.1.1.1 through which a distal tip 3.1.1 of the needle 3.1 protrudes when the needle assembly 3 is coupled to the needle hub 1. The proximal end 1.1.4 includes a coupling arrangement for engaging the delivery device 2. For example, the coupling arrangement may be a screw thread 1.1.6 which is adapted to engage a corresponding screw thread 2.1 on the delivery device 2. In other exemplary embodiments, the coupling arrangement may include a bayonet coupling, a snap-fit, a friction fit, etc. A proximal tip 3.1.2 of the needle 3.1 is adapted to be inserted into a cartridge or container containing the medicament in the delivery device 2 when the needle hub 1 is coupled to the delivery device 2. When the needle hub 1.1 is coupled to the delivery device 2, the shoulder 1.1.5 may abut a distal end of the delivery device 2.

In an exemplary embodiment, the needle hub 1 includes a needle assembly engagement mechanism F1 adapted to releasably engage the needle assembly 3. The needle assembly engagement mechanism F1 includes two or more resilient arms 1.1.2 disposed on the housing 1.1 and extending in a distal direction D from the shoulder 1.1.5. In a first (non-deflected state), distal ends of the arms 1.1.2 form an aperture 1.1.2.1 adapted to receive the needle assembly 3. When engaging the needle assembly 3 to the needle hub 1, the needle assembly 3 is pushed into engagement with the arms 1.1.2, and the retainer element 3.3 causes the arms 1.1.2 to deflect radially. When the retainer element 3.3 reaches notches formed in the arms 1.1.2, the arms 1.1.2 return to their non-deflected position and engage the needle assembly 3. For example, as shown in FIG. 1, the notches abut the distal part 3.3.1 of the retainer element 3.3.

In an exemplary embodiment, the needle hub 1 further includes a spring 1.2 adapted to apply a biasing force to the needle assembly 3 when it is coupled to the needle hub 1. The spring 1.2 may be disposed in a channel 1.1.3 between the arms 1.1.2. In an exemplary embodiment, a diameter of the channel 1.1.3 is less than a diameter of the aperture 1.1.2.1 to facilitate insertion of the needle assembly 3 into the needle hub 1. The spring 1.2 may be grounded distally on the notches in the arms 1.1.2 and proximally on a bearing surface 1.1.5.1 on the shoulder 1.1.5. As shown in FIG. 1, the bearing surface 1.1.5.1 includes a through hole for allowing the proximal tip 3.1.2 of the needle 3.1 to pass through when the needle assembly 3 is coupled to the needle hub 1.

When the needle assembly 3 is coupled to the needle hub 1, the retainer element 3.3 may engage and compress the spring 1.2. For example, the proximal part 3.3.2 of the retainer element 3.3 may fit axially within coils of the spring 1.2, and the distal part 3.3.1 may bear on the spring 1.2. Thus, when the needle assembly 3 is coupled to the needle hub 1, as shown in FIG. 1, the spring 1.2 may apply a biasing force in the distal direction on the needle assembly 3.

In another exemplary embodiment, the spring 1.2 may be part of the needle assembly 3. For example, the proximal part 3.3.2 of the retainer element 3.3 may be formed as the spring 1.2, e.g. one moulded part, especially injection-moulded part made from polypropylene.

Figure 4:
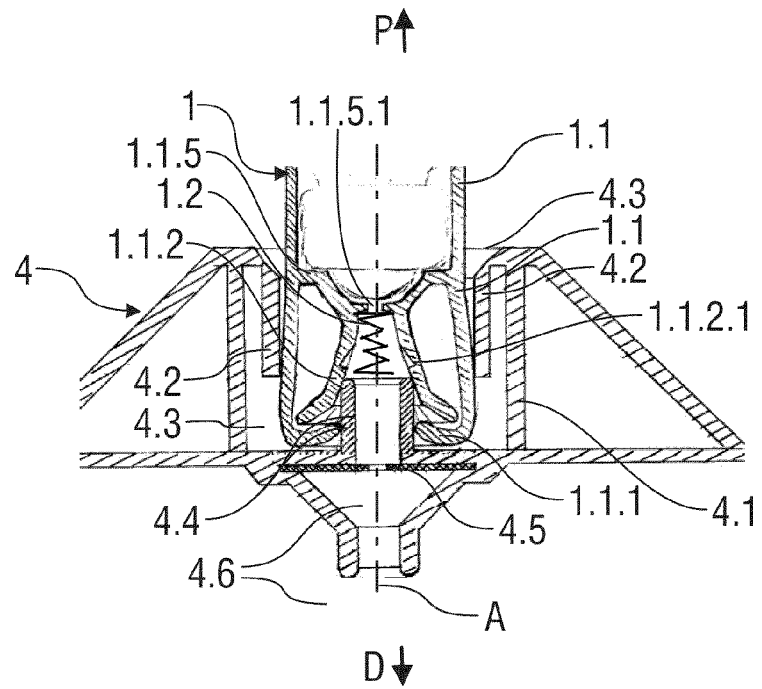
FIG. 4 shows a sectional view of a part of an exemplary embodiment of a needle assembly disposal device according to the present invention.

FIG. 4 shows an exemplary embodiment of a needle assembly disposal device 4 according to the present invention. The disposal device 4 is formed as a container having a housing 4.1. The housing 4.1 includes an interface 4.2 adapted to disengage the needle assembly 3 from the needle hub 1. In an exemplary embodiment, the interface 4.2 includes an opening 4.3 adapted to receive the needle hub 1. The interface 4.2 may further include alignment features adapted to abut an outer surface of the housing 1.1 of the needle hub 1 so that the needle hub 1 and the needle assembly 3 are properly oriented on the disposal device 4.

When the needle hub 1 is inserted into the opening 4.3, the distal tip 3.1.1 of the needle 3.1 passes through a stem 4.4 disposed over an opening to a cavity 4.6 in the disposal device 4. A base of the stem 4.4 may at least partially covered by a flexible membrane 4.5 having an expandable aperture initially sized to receive the needle 3.1 but expandable to receive the retainer element 3.3.

As the needle hub 1 is further inserted into the opening 4.3, the stem 4.4 is inserted into aperture 1.1.2.1 and then the channel 1.1.3 between the arms 1.1.2, causing the arms 1.1.2 to deflect radially. As the arms 1.1.2 deflect, the notches release the retainer element 3.3, and the biasing force of the spring 1.2 pushes the needle assembly 3 in the distal direction relative to the needle hub 1. The force of the spring 1.2 pushes the needle assembly 3 through the membrane 4.5 and into the cavity 4.6. The retainer element 3.3 may cause the membrane 4.5 to deflect in the distal direction, stretching and expanding the aperture in the membrane 4.5 and allowing the retainer element 3.3 to pass through. Once the retainer element 3.3 has passed through the aperture in the membrane 4.5, the aperture may return to its initial size and prevent the needle assembly 3 from through the membrane in the proximal direction because the membrane 4.5 cannot deflect in the proximal direction (it will abut the housing 4.1).

Figure 5:
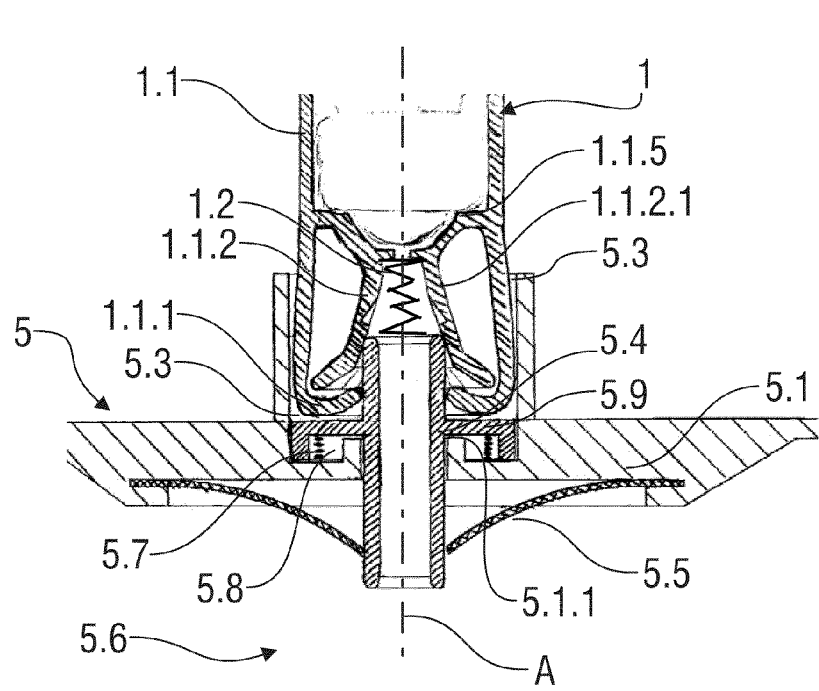
FIG. 5 shows a sectional view of a part of another exemplary embodiment of a needle assembly disposal device according to the present invention.

FIG. 5 shows another exemplary embodiment of a needle assembly disposal device 5 according to the present invention. The disposal device 5 is formed as a container having a housing 5.1. The housing 5.1 includes an interface adapted to disengage the needle assembly 3 from the needle hub 1. In an exemplary embodiment, the interface includes an opening 5.3 adapted to receive the needle hub 1. The interface may further include alignment features adapted to abut an outer surface of the housing 1.1 of the needle hub 1 so that the needle hub 1 and the needle assembly 3 are properly oriented on the disposal device 5.

When the needle hub 1 is inserted into the opening 5.3, the distal tip 3.1.1 of the needle 3 passes through a stem 5.4 disposed over an opening to a cavity 5.6 in the disposal device 5. A base of the stem 5.4 may be at least partially covered by a flexible membrane 5.5 having an expandable aperture initially sized to receive the stem 5.4.

In this exemplary embodiment, the stem 5.4 may be coupled to the housing 5.1 via a spring 5.7 which is ground distally on the housing 5.1 and proximally on a connector 5.9 which is coupled to the stem 5.4. The spring 5.7 may be disposed in a cavity 5.8 formed on a surface of the housing 5.1. The spring 5.7 may apply a force on the connector 5.9 to bias the stem 5.4 in the proximal direction.

As the needle hub 1 is further inserted into the opening 5.3, the distal end 1.1.1 of the housing 1.1 abuts the connector 5.9, pushing the stem 5.4 in the distal direction and compressing the spring 5.7. When the stem 5.4 abuts the housing 5.1, the stem 5.4 is inserted into aperture 1.1.2.1 and then the channel 1.1.3 between the arms 1.1.2, causing the arms 1.1.2 to deflect radially. As the arms 1.1.2 deflect, the notches release the retainer element 3.3, and the biasing force of the spring 1.2 pushes the needle assembly 3 in the distal direction relative to the needle hub 1. The force of the spring 1.2 pushes the needle assembly 3 through the stem 5.4 and into the cavity 5.6. The stem 5.4 may cause the membrane 5.5 to deflect in the distal direction, stretching and expanding the aperture in the membrane 5.5 and allowing the stem 5.4 to pass through. Once the needle hub 1 has been removed from the disposal device 5, the stem 5.4 may return to an extended position under the biasing force of the spring 5.7, and the aperture in the membrane 5.5 may return to its initial size and prevent the needle assembly 3 from through the membrane in the proximal direction because the membrane 5.5 cannot deflect in the proximal direction (it will abut the housing 5.1).

Those of skill in the art will understand that the needle assembly disposal devices 4, 5 allow a removal of used needle assemblies 3 safely and easily from the needle hub 1 and reliably stow them away to protect users from needle sticks or accidental re-use of used needles 3.1 by which a transfer of diseases such as Hepatitis or HIV is possible.

Figure 3:
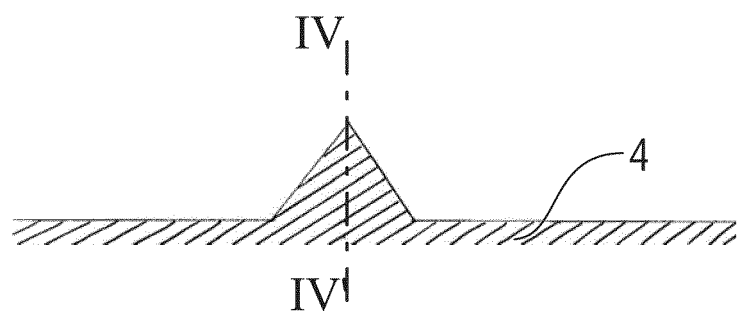
FIG. 3 shows schematically a sectional view of a part of an exemplary embodiment of a needle assembly disposal device according to the present invention.

FIG. 3 show an exemplary embodiment of a deflector that may be utilized within a housing 4.1, 5.1 of a needle assembly disposal device 4, 5. The deflector may be a conical protrusion which is disposed underneath the interface 4.2. After the needle assembly 3 disengages the needle hub 1, the distal tip 3.1.1 of the needle 3.1 impacts the deflector and causes the needle assembly 3 to be disposed at an angle in the disposal device 4, 5. Thus, the deflector may prevent used needle assemblies in the disposal device from blocking other used needle assemblies from being disposed in the disposal device.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle hub comprising:
    a proximal end adapted to engage a medicament delivery device;
    a distal end having an opening;
    a shoulder disposed between the proximal end and the distal end; and
    a needle assembly engagement mechanism coupled to the shoulder and adapted to releasably engage a needle assembly, the needle assembly engagement mechanism including two or more resilient arms adapted to releasably engage a retainer element on the needle assembly, the two or more resilient arms defining therebetween a channel adapted to receive a proximal part and a distal part of the retaining element.

2. The needle hub according to claim 1, wherein the proximal end includes a screw thread.

3. The needle hub according to claim 1, wherein the arms include notches adapted to engage the retainer element when the arms are in a non-deflected position.

4. The needle hub according to claim 3, wherein a spring disposed between the arms and grounded proximally on the shoulder is grounded distally on the notches when the arms are in the non-deflected position.

5. The needle hub according to claim 1, wherein the channel has a first diameter, an aperture having a second diameter is formed at a distal end of the arms, and the second diameter is greater than the first diameter.

6. The needle hub according to claim 1, further comprising:
    a spring disposed between the arms and grounded proximally on the shoulder.

7. The needle hub of claim 6, wherein, during engagement of the needle assembly engagement mechanism and the needle assembly, the arms are biased against the retainer element and the spring bears against the needle assembly in a distal direction
    wherein the needle assembly engagement mechanism is releasable by an outward bending of the arms, and the needle assembly is released and pushed distally by relaxing of the spring.

8. A needle assembly for use with a needle hub, the needle assembly comprising:
    a needle having a distal tip and a proximal tip; and
    a retainer element disposed on the needle, the retainer element being configured to be releasably engaged by two or more resilient arms, the needle hub comprising a proximal end adapted to engage a medicament delivery device, a distal end having an opening, a shoulder disposed between the proximal end of the needle assembly and the distal end of the needle assembly, and a needle assembly engagement mechanism coupled to the shoulder and comprising the two or more resilient arms,
    wherein the retainer element has a distal part with a third diameter and a proximal part with a fourth diameter, wherein the third diameter is greater than the fourth diameter.

9. The needle assembly according to claim 8, wherein the third diameter is substantially equal to a second diameter of an aperture formed at a distal end of the arms of the needle assembly engagement mechanism and the fourth diameter is substantially equal to a first diameter of a channel disposed between the arms of the needle assembly engagement mechanism.

10. The needle assembly according to claim 8, wherein the fourth diameter is less than a diameter of a spring disposed between the arms of the needle assembly engagement mechanism and grounded proximally on the shoulder of the needle hub.

11. The needle assembly according to claim 8, wherein, when the needle assembly is retained in the needle hub, the distal part of the retainer element is configured to abut notches of the arms.

12. The needle assembly of claim 8, wherein the retainer element is configured to compress a spring of the needle hub when the needle assembly is coupled to the needle hub.

13. The needle assembly of claim 8, the retainer element is sized and dimensioned such that both of the proximal part and the distal part of the retainer element are configured to be received by a channel defined between the arms of the needle assembly engagement mechanism.

14. The needle assembly of claim 8, wherein, during engagement of the needle assembly engagement mechanism and the needle assembly, the retainer element bears against the arms in a radial direction and bears against a spring in a proximal direction, wherein the retainer element is released and pushed distally by relaxing of the spring when the needle assembly engagement mechanism is released by an outward bending of the arms.

15. A needle assembly disposal device, the disposal device comprising:

a housing having a cavity therein;

an interface disposed on the housing and having an opening adapted to receive a needle hub, the needle hub comprising a proximal end adapted to engage a medicament delivery device, a distal end having an opening, a shoulder disposed between the proximal end and the distal end, and a needle assembly engagement mechanism coupled to the shoulder and adapted to releasably engage a needle assembly;

a stem adapted to engage two or more resilient arms of the needle assembly engagement mechanism, the arms being adapted to releasably engage a retainer element on the needle assembly; and a flexible membrane disposed adjacent a base of the stem, the membrane having an expandable aperture.

16. The needle assembly disposal device according to claim 15, wherein the interface includes alignment features adapted to align the needle hub with the stem.

17. The needle assembly disposal device according to claim 15, further comprising:

a spring applying a biasing force to the stem, the spring grounded distally on the housing and proximally on a connector coupled to the stem.

18. The needle assembly disposal device according to claim 15, further comprising:

a deflector disposed within the housing and aligned with the stem.

19. The needle assembly disposal device of claim 15, wherein the stem is configured to be inserted into a channel defined between the arms of the needle assembly engagement mechanism to cause the arms to deflect radially, thereby releasing at least a distal part of the retainer element from the arms.

20. The needle assembly disposal device of claim 15, wherein, when the needle assembly engagement mechanism is engaged to the needle assembly, the stem is configured to cause an outward bending of the arms to release the needle assembly engagement mechanism from the needle assembly such that the needle assembly is pushed distally by relaxing of a spring of the needle assembly.

* * * * *